United States Patent [19]

Lehneis et al.

[11] Patent Number: 4,614,518

[45] Date of Patent: Sep. 30, 1986

[54] ARTIFICIAL LIMB WITH AUTOMATIC RELEASE FOR FREE ROTATION

[75] Inventors: Hans R. Lehneis, Roslyn; Charles Reibel, New York, both of N.Y.

[73] Assignee: New York University, New York, N.Y.

[21] Appl. No.: 473,335

[22] Filed: Mar. 8, 1983

[51] Int. Cl.[4] ............................................. A61F 2/62
[52] U.S. Cl. ..................................................... 623/39
[58] Field of Search ..................... 3/26, 24, 12, 22, 29, 3/2

[56] References Cited

U.S. PATENT DOCUMENTS

| | | | |
|---|---|---|---|
| 2,573,347 | 7/1947 | Mazzola | 3/24 |
| 2,661,479 | 12/1953 | Alderson | 3/12 |
| 3,351,955 | 11/1967 | Middleton | 3/22 |
| 3,833,942 | 9/1974 | Collins | 3/29 |
| 4,232,405 | 11/1980 | Janovsky | 3/26 |
| 4,520,512 | 6/1985 | Lehneis et al. | 3/2 |

Primary Examiner—Richard J. Apley
Assistant Examiner—James Prizant
Attorney, Agent, or Firm—Darby & Darby

[57] ABSTRACT

An artificial limb having two limb members connected by a joint is provided with rotator members, comprising one of the limb members, which are relatively rotatable about an axis extending along the limb. The rotator members are generally cylindrical, with the outer one forming a rotatable sleeve about the inner one. One of the rotator members has a concentric radially extending flange with an opening near the perimeter. A locking mechanism is provided on the other rotator member which is movable from a locking position to a released position. In the locking position, the locking mechanism provides a rigid connection between the two rotator members by inserting a plunger in the opening, thereby preventing rotation between the rotator members. When moved to its released position, the locking mechanism removes the plunger from the opening, thereby permitting relative rotation between rotator members. The locking member is disposed on one limb member in the vicinity of the joint and is connected via a coupling member to a fixed connection point on the other limb member. Normal movement of the limb about the joint thereby achieves movement of the locking mechanism between its locking and released positions, via the coupling member, and achieves automatic release and locking of the limb with respect to rotation the limb is bent and straightened.

16 Claims, 6 Drawing Figures

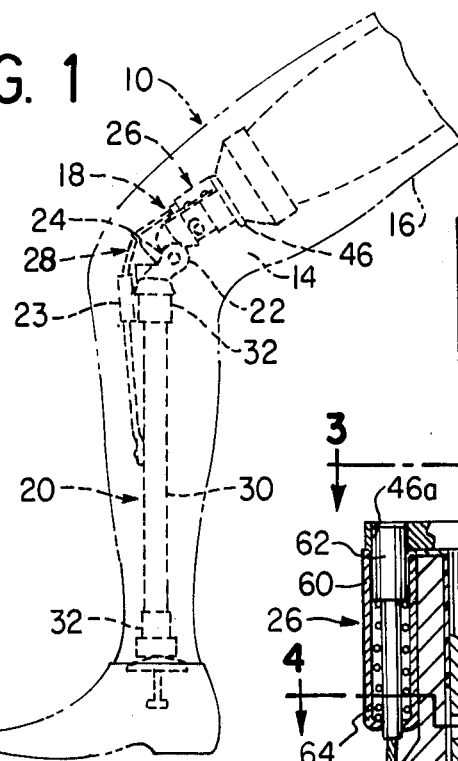
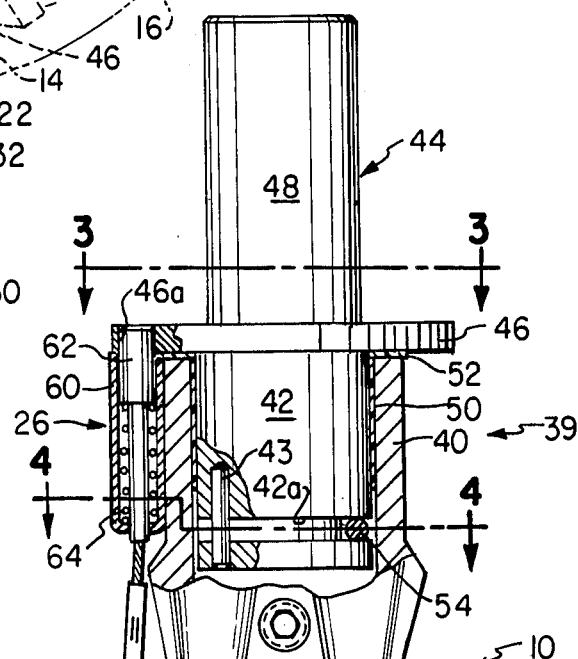
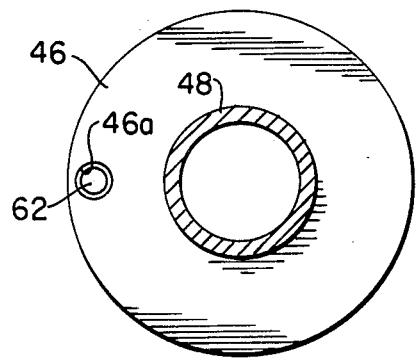
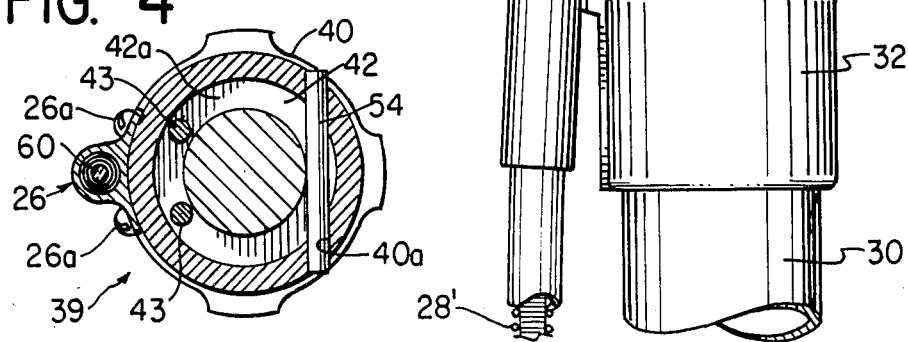

ARTIFICIAL LIMB WITH AUTOMATIC RELEASE FOR FREE ROTATION

The present invention relates generally to artificial limbs and, more particularly, concerns an artificial limb construction which is normally rigid, except for pivotal movement about the joints, and is actuated by the normal movement about one of the joints to enable and disable free rotation of the limb about an axis extending along its length.

Modern prostheses, such as artificial limbs, have enabled handicapped individuals to lead rather normal, productive lives. By providing an amputee with an artificial limb that simulates the operation of a real limb, it is possible, not only to enable him to perform his day-to-day tasks, but also to help him avoid the social embarrassments occasioned by his being recognized as an amputee.

In the past, those individuals with radical amputations have been unable to obtain entirely effective artificial limbs. For example, a patient whose leg has been amputated to a point above the knee joint would normally receive a prosthesis with an artificial knee joint and a lower leg, as well as a thigh portion having a "socket" in which the stump of his residual leg is securely received. Owing to the lack of a physical connection between the prosthesis and the patient's thigh bone, the patient cannot transmit rotation of the hip joint to the prosthesis. As a result, the patient is unable to achieve any appreciable rotation of the artificial limb about an axis extending along the thigh. This makes it impossible for the patient to dress the prosthetic leg completely while wearing it. The patient is also unable to perform certain normal movements, such as assuming a crossed-leg position while sitting, and he experiences great difficulty getting in and out of an automobile.

In an attempt to overcome the difficulties which radical amputees experience with prosthetic legs, such devices have been provided with units permitting rotation of the leg about an axis extending along the thigh. Typically, such units, called femoral rotator units, are provided in the vicinity of the knee joint and directly above it. Inasmuch as the artificial leg must support the patient when he walks, it is extremely important that no rotary movement take place while he walks. The rotator unit is therefore provided with a locking mechanism which must be released by the patient when he wishes to rotate the leg about the thigh. This has been achieved by providing a release button at the side of the leg, which the patient operates when he wishes to rotate the leg about the thigh. Although this releasable thigh rotator unit provides relief for the loss of normal hip rotation, it is hardly a satisfactory solution to the problem, since the patient must fumble with his leg to locate the release/lock button whenever he wishes to rotate the leg. This is not only inconvenient, but can prove socially embarrassing.

Similar rotator units have been provided for patients whose arms have been amputated to a point above the elbow joint, in order to permit rotation about an axis extending along the upper arm (humeral rotation). In such humeral rotator units, locking and unlocking for rotation has been achieved by means of a cable which is connected from the rotator unit, across the patient's back, to the opposite shoulder. By moving the opposite shoulder, the patient can then lock and unlock the humeral rotator for rotation. This type of device is also not entirely satisfactory, because it requires some conscious movement on the part of the wearer in order to lock and unlock the unit for rotation. This not only proves to be an inconvenience, but an embarrassment, since the patient can easily be identified as an amputee by the unusual shoulder movements required to achieve release and locking of the limb for rotation.

In copending U.S. patent application Ser. No. 300,256, now U.S. Pat. No. 4,520,512, assigned to the assignee of the present application, there is disclosed an artificial limb which can be automatically released for rotation about an axis extending along the length of the limb by normal movement (e.g. bending) of the limb. An artifical limb having two limb members connected by a joint is provided with rotator members, comprising one of the limb members, which members are relatively rotatable about an axis extending along the limb. A locking mechanism is provided which is movable from a locked position to a released position. In the locked position, the locking mechanism provides a rigid connection between the two rotator members and thereby prevents limb rotation. When moved to its released position, the locking mechanism is disengaged from at least one of the rotator members, thereby permitting relative rotation between them. The locking member is disposed on one limb member in the vicinity of the joint and is connected via a coupling member to a fixed connection point on the other limb member. Normal movement of the limb about the joint thereby achieves movement of the locking mechanism between its locking and released positions, via the coupling member, and achieves automatic release and locking of the limb with respect to rotation, as the limb is bent and straightened.

In one embodiment of the invention of patent application Ser. No. 300,256, now U.S. Pat. No. 4,520,512, identified as an endoskeletal artificial leg, a femoral rotator was provided which was compatable with a modular system of endoskeletal prosthesis components which is available from Otto Bock Orthopedic Industry, Inc. of Minneapolis Minn. The femoral rotator comprised two telescoped cylindrical members which provided relative rotation at the thigh, and a spring loaded slide member which was moveable from a position where it provided a solid connection between the two members to a position where it released the two members for relative rotation. Although this femoral rotator was found to work effectively and reliably, its construction proved somewhat too complex for efficient commercial production. Also, the rotator was quite long, so it could not be used by patients with thigh amputations close to the knee, in which case the patient's "stump" extended too closely to the knee joint to accommodate the rotator.

Broadly, it is an object of the present invention to provide an artificial limb having a rotator unit providing rotation about an axis extending along the limb, in which limb the unit may be enabled or disabled for rotation when certain predefined, normal movements of the limb itself are performed.

It is also an object of the present invention to provide an automatically operable rotator unit which can readily be incorporated into existing artificial limb constructions with a minimum of modifications.

It is a further object of the present invention to provide an artificial limb with an automatically lockable and releasable rotator unit which is convenient and reliable in use, yet relatively simple and inexpensive in construction.

It is a specific object of the present invention to provide a rotator unit for a modular endoskeletal prosthesis which can be released for rotation by normal movements of the limb and which is so constructed as to be amenable to manufacture by known commercial processes.

It is also a specific object of the present invention to provide a rotator unit of the type described which can fit in a relatively small space between a joint of the prosthesis and the patient's "stump" so as to permit its use by a patient with an amputation close to the patient's joint.

In accordance with a preferred embodiment of the present invention an artificial limb having two limb members connected by a joint is provided with rotator members, comprising one of the limb members, which are relatively rotatable about an axis extending along the limb. The rotator members are generally cylindrical, with the outer one forming a rotatable sleeve about the inner one. One of the rotator members has a concentric radially extending flange with an opening near the perimeter. A locking mechanism is provided on the other rotator member which is movable from a locking position to a released position. In the locking position, the locking mechanism provides a rigid connection between the two rotator members by inserting a plunger in the opening, thereby preventing rotation between the rotator members. When moved to its released position, the locking mechanism removes the plunger from the opening, thereby permitting relative rotation between rotator members. The locking member is disposed on one limb member in the vicinity of the joint and is connected via a coupling member to a fixed connection point on the other limb member. Normal movement of the limb about the joint thereby achieves movement of the locking mechanism between its locking and released positions, via the coupling member, and achieves automatic release and locking of the limb with respect to rotations the limb is bent and straightened.

The foregoing brief description, as well as further objects, features and advantages of the present invention will be more completely understood from the following detailed description of a presently preferred, but nonetheless illustrative, embodiment of the present invention, with reference being had to the accompanying drawing, wherein:

FIG. 1 is a side elevational view of an artificial leg embodying the present invention, the leg being shown in a partially bent position;

FIG. 2 is an elevational view, similar to FIG. 1 but on an enlarged scale, in which the inner mechanism of the leg in the vicinity of the knee joint is shown with the leg in an upright position;

FIG. 3 is a sectional view taken along contour 3—3 in FIG. 2 and looking in the direction of the arrows;

FIG. 4 is a sectional view taken along contour 4—4 in FIG. 2 and looking in the direction of the arrows;

DETAILED DESCRIPTION

Figure 5:
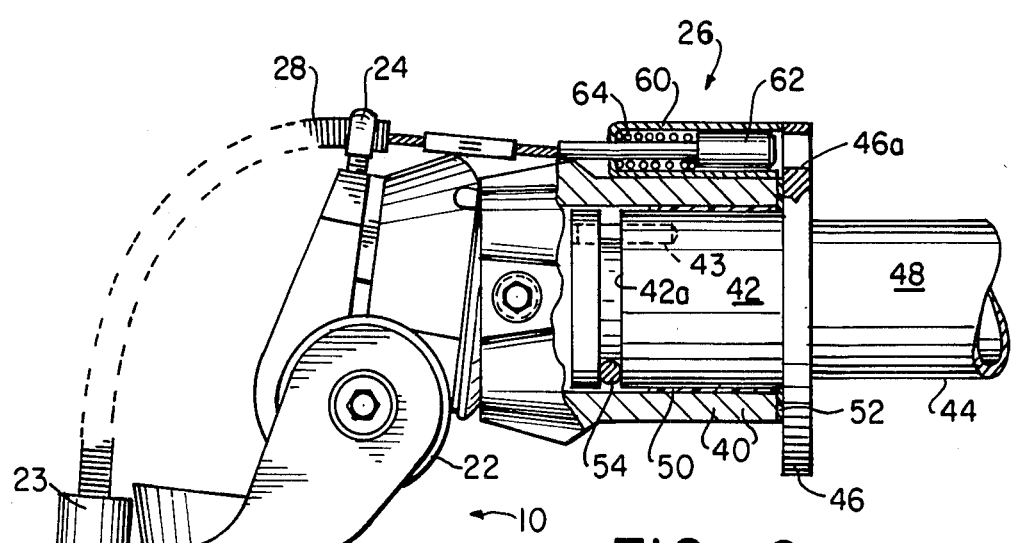
FIG. 5 is an elevational view similar to FIG. 2 in which the inner mechanism of the leg in the vicinity of the knee joint is shown with the leg bent to an angle of approximately 90 degrees.
Figure 6:
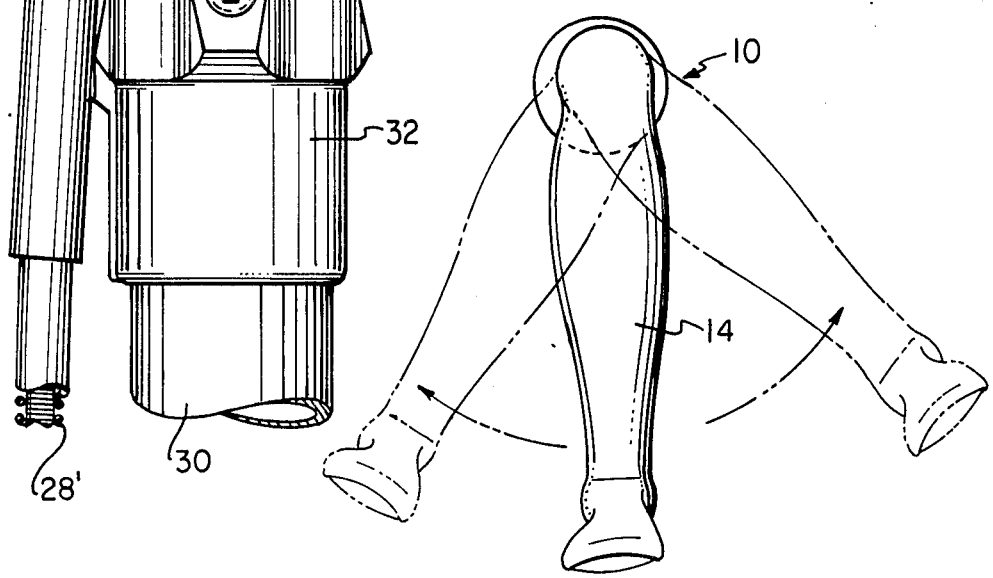
FIG. 6 is a front elevational view of the leg of FIGS. 1-5 illustrating the manner in which the leg may be rotated about the thigh when it is brought to the bent position shown in FIG. 5.

Two broad categories of artificial limbs or prostheses are generally known: the exoskeletal type and the endoskeletal type. An exoskeletal limb is formed with a hard outer shell which is shaped to simulate a real limb and is generally hollow. In an exoskeletal artificial leg, for example, the shell serves to support the wearer and to house the internal mechanisms of the leg. An endoskeletal prosthesis includes elongated, internal supporting members, similar to human bones, which are embedded in a foam material and covered by a resilient, flesh-like sheathe or stocking to simulate the appearance of a human limb. In an endoskeletal artificial leg, the structural members support the wearer, as well as all related mechanisms, and the foam and covering sheath conceal the structural members and mechanisms to lend a realistic appearance to the artificial limb. The present invention is applicable to endoskeletal limbs.

The figures illustrate an endoskeletal prosthesis in the form an artificial leg 10 embodying the present invention. The the prosthesis 10 is intended for use by a patient with a leg which has been amputated to a point above the knee.

The prosthesis 10 is constructed so as to be compatable with a modular system of endoskeletal prosthesis components which is available from Otto Bock Orthopedic Industry Inc. of Minneapolis, Minn. As is characteristic of endoskeletal devices, the prosthesis 10 has an internal framework 12 simulating the bones forming the skeletal structure of the human leg. This framework is embedded in a mass of foam material or padding 14 which fills in the shape of the leg and lends a human "softness" to it. The padding 14 is then surrounded by a sheath of flexible material 16 forming the "outer skin" of the leg.

The framework 12 broadly comprises: a thigh unit 18 incorporating a femoral rotator mechanism described in detail below; a lower leg unit 20 including an artificial foot; and a knee joint unit 22 connecting the units 18 and 20 for relative pivotal movement. The prosthesis 10 also includes a locking mechanism 26 mounted on the thigh unit which normally locks the femoral rotator against movement, but is actuable through a coupling member 28, to release the femoral rotator for rotation. The coupling member 28 is supported on guides 23 and 24 provided on knee joint unit 22, below and above the joint respectively, and passes across the knee joint for connection to the lower leg unit by a conventional clamping means. Prosthesis 10 achieves automatic releasing and locking of the femoral rotator with bending and straightening of the leg 10 at the knee joint.

The lower leg unit 20 is entirely a standard Otto Bock assembly. It comprises an elongated tube 30 having a tube clamp 32 secured at either end. The lower tube clamp receives an ankle and foot unit for securement to tube 30, and the upper tube clamp (modified by having the guide 23 secured thereto) joins the knee joint unit 22 and the tube 30.

The knee joint unit 22 is also a standard Otto Bock unit, but it is modified by the addition of the support and guide 24 for connecting member 28 which keeps the connecting member at a distance from the knee joint and also prevents it from moving laterally with respect to the leg.

The thigh unit 18 includes: a cup-shaped member 35 (a standard Otto Bock component), which is laminated into the lower end of the leg socket which receives the patient's stump; and a femoral rotator unit 39 having an Otto Bock tube clamp at either end. The lower tube clamp is slightly modified, as will be explained below, and serves to join the knee joint to the rotator unit. The upper tube clamp is used in the conventional manner to join the cup-shaped member 35 and the rotator unit 39.

As best seen in FIG. 2, the lower tube clamp 40 serves as a sleeve which is mounted for rotation on a lower shaft portion 42 of a core subassembly 44. Core subassembly 44 further includes a concentric flange portion 46 and an upper shaft portion 48. Between the shaft portion 42 and the interior wall of tube clamp 40, there is provided a bearing sleeve 50, and between the upper surface of the tube clamp and the lower surface of the flange 46 there is provided a bearing disc 52. The sleeve 50 and disc 52 may be made, for example, of teflon, in order to minimize friction when relative rotation occurs between the core subassembly 44 and the tube clamp 40.

Tube clamp 40 is a standard Otto Bock tube clamp (similar to tube clamp 32) which has been modified in two principal ways. First of all, the locking mechanism 26 has been added and is secured to tube clamp 40, for example, by means of bolts 26a. Secondly, opposed bores 40a, 40a are provided, into which a laterally disposed pin 54 is press fitted for a purpose to be discussed below.

Locking member 26 broadly comprises: a cylindrical housing 60; a plunger 62 mounted for sliding movement within housing 60 and protruding through the bottom thereof to have coupling member 28 secured thereto; and a compression spring 64 interposed between the plunger 62 and the bottom of the housing 60 so as to urge the plunger up with respect to the housing. In addition, plunger 62 is retained within housing 60 by conventional means, not shown. While so retained, the upper portion of plunger 62 protrudes above the housing 60, as shown in FIG. 2.

Core subassembly 44 is preferably made of a sturdy metal, such as steel. This subassembly is machined so that the shaft portion 42 and the under surface of flange 46 are smooth, and so that portions 42, 46 and 48 are concentric. Lower shaft portion 42 is dimensioned to be received securely within tube clamp 42, yet so as to permit free rotation thereof within the sleeve 50. Lower shaft portion 42 has a circumferential groove 42a which is positioned to receive the lateral pin 54. Groove 42a is dimensioned to receive the pin 54 securely, yet to permit it to slide freely within the groove. In addition, the lower shaft portion includes a pair of upright pins 43, 43, which serve to limit the rotational movement of tube clamp 40 about shaft 42. Referring to FIG. 4, it will be appreciated that the upper pin 43 limits the counterclockwise rotation of sleeve 40 when this pin comes into contact with pin 54, and that the lower pin 43 similarly limits the clockwise rotation of sleeve 40 when it comes into contact with pin 54. The pins 43, 43 are inserted in respective bores in the shaft portion 42 through the bottom thereof and are preferably retained therein as a result of an interference fit.

Flange portion 46 has a through-bore 46a near its perimeter which is axially aligned with flange portion 46. Bore 46a is dimensioned to receive the upper end of plunger 62 therein for free sliding movement. The shaft portion 48 is dimensioned to be received within a tube clamp and, by means of the upper tube clamp on rotator unit 39, is secured against rotation with respect to the cup-shaped member 35.

In assemblying the rotator unit 39, the bearing disc 52 is placed in contact with the bottom of flange portion 46 and sleeve member 50 is slipped onto shaft portion 42 and urged into contact with the bottom of bearing disc 52. Shaft portion 42 is then inserted into tube clamp 40 and pressed downward until the bottom of disc 52 is in contact with the top of tube clamp 40. Pin 54 is then pressed into the bores 40a, 40a and is retained therein as a result of an interference fit. Pin 54 is captured within groove 42a of shaft portion 42 and retains the shaft portion against removal from within tube clamp 40. Cup-shaped member 35 may then be joined to upper shaft portion 48 by means of the upper tube clamp.

The normal or straightened position of the prosthesis 10 is depicted in FIG. 2. As shown, the pressure of spring 64 then urges the plunger 62 into the bore 46a of flange portion 46. This serves to lock tube clamp 40 and shaft portion 42 together so as to prevent relative rotation therebetween. The entire prosthesis above the knee joint then acts as one solid member to permit normal walking.

When the prosthesis 10 is bent at the knee joint to approximately a right angle, operation is as depicted in FIG. 5. Plunger 62 is then pulled by coupling member 28 and withdrawn from bore 46a against the pressure of spring 64, which is compressed. Tube clamp 40 is then free to rotate about shaft portion 42, while shaft portion 48 is securely retained with respect to the cup-shaped member 35 (and therefore with respect to the patient's stump). This permits free rotation of the lower leg with respect to the thigh.

When prosthesis 10 is returned to its upright position or is otherwise straightened, the force applied to plunger 62 by coupling member 28 is reduced, and spring 64 urges the plunger back towards flange portion 46. If the prosthesis 10 is then in a non-rotated position, the plunger 62 will be aligned with the aperture 46a, the plunger will enter the aperture and will lock together tube clamp 40 and core subassembly 44 to prevent relative rotation therebetween. Should the prosthesis be in a rotated position, the top of plunger 62 will be urged against the bottom surface of flange portion 46. When the prosthesis 10 is subsequently returned to its non-rotated position, plunger 62 will enter aperture 46a immediately, thereby locking up femoral rotator 39 against rotation.

From the foregoing description, it will be appreciated that the present invention provides an endoskeletal prosthetic limb which is automatically released and locked for rotation about an axis extending along its length by the normal bending movement of the limb. Moreover, no conscious action is required by the patient in order to achieve the release and locking, eliminating any inconvenience and embarrassment for the patient.

It will be appreciated that the upper tube clamp of femoral rotator 39 could be eliminated if the cup-shaped member were adapted to receive upper shaft portion 48 directly.

Although a preferred form of the invention has been disclosed for illustrative purposes, those skilled in the art will appreciate that many additions, modifications and substitutions are possible without departing from the scope and spirit of the invention a defined by the accompanying claims.

What is claimed is:

1. In an artificial limb including first and second limb members connected for relative pivotal movement about a joint member, a rotator assembly for achieving rotation of said first limb member about an axis extending along its length, said rotator assembly being automatically enabled and disabled for rotation by the relative pivotal movement of said limb members, said rotator assembly comprising:

first and second rotator members on said first limb member mounted to be relatively rotatable about said axis, said rotator members being generally cylindrical and coaxially mounted extending within said second rotator member, one of said rotator members having a radially extending flange of substantially larger diameter than said rotator members, with an axially directed opening therein;

locking means, movable between a locking position and a released position, for providing a rigid connection between said rotator members when in said locking position, thereby preventing relative rotation thereof, said locking means being disengaged from at least one of said rotator members when in said released position, thereby permitting relative rotation thereof said locking means comprising a plunger mounted on the other of aid rotator members for movement towards and away from said opening, said plunger extending into said opening in said locking position and being external of said opening in said released position;

coupling means extending across said joint for providing a mechanical connection between said locking means and a fixed point on said second limb member, and means for transmitting to said coupling means relative pivotal movement of said limb members, to impart to said locking means movement thereof between said locking and released positions.

2. An artificial limb in accordance with claim 1 wherein said first rotator member is said one rotator member and includes a circumferential groove remote from said flange, said limb further comprising a pin extending through said second rotator member into said groove, said pin being dimensioned to move freely within said groove, whereby said first rotator member is retained against removal from within said second rotator member, but is capable of being rotated freely therein.

3. An artificial limb in accordance with claim 1 wherein said flange is provided on said first rotator member and is substantially disc-shaped, said first rotator member further comprising first and second cylindrical portions projecting coaxially from either side of said flange, one of said cylindrical portions extending within said second rotator member.

4. An artificial limb in accordance with claim 1 wherein said coupling means includes a first resilient member applying a force to said locking means to achieve movement thereof between said locking and released positions, said force being produced by stressing said resiient member as a result of the relative pivotal movement of said limb members.

5. An artificial limb in accordance with claim 1 wherein said coupling means includes a tension spring forming at least a portion of an elongated coupling member extending across said joint member, said coupling member being positioned so that no appreciable tensioning of said spring occurs when said limb is straightened, but substantial tensioning thereof occurs when said limb is bent about said joint.

6. An artificial limb in accordance with claim 1 wherein said artificial limb is an artificial leg and said joint is a knee joint.

7. An artificial limb in accordance with claim 2 wherein said flange is provided on said first rotator member and is substantially disc-shaped, said first rotator member further comprising first and second cylindrical portions projecting coaxially from either side of said flange, one of said cylindrical portions extending within said second rotator member.

8. An artificial limb in accordance with claim 2 wherein said first rotator member further comprises at least one additional pin extending generally parallel to said axis through said circumferential groove, said at least one additional pin acting as stop means to limit the angle of relative rotation between said first and second rotator members.

9. An artificial limb in accordance with claim 4 wherein said locking means includes second resilient means providing a force opposing the force of said first resilient members.

10. An artificial limb in accordance with claim 4 wherein said artificial limb is an artificial leg and said joint is a knee joint.

11. An artificial limb in accordance with claim 8 wherein said flange is provided on said first rotator member and is substantially disc-shaped, said first rotator member further comprising first and second cylindrical portions projecting coaxially from either side of said flange, one of said cylindrical portions extending within said second rotator member.

12. An artificial limb in accordance with claim 9 wherein said artificial limb is an artificial leg and said joint is a knee joint.

13. In an artificial limb including first and second limb members connected for relative pivotal movement about a joint member, a rotator assembly for achieving rotation of said first limb member about an axis extending along its length, comprising first and second, generally cylindrical rotator members on said first limb member coaxially mounted for rotation about said axis with said first rotator member extending within said second rotator member, said first rotator member including a circumferential groove axially positioned to be located within said second rotator member, pin means extending through said second rotator member into said groove, said pin means being dimensioned to move freely within said groove, whereby said first rotator member is retained against removal from within said second rotator member, but is capable of being rotated freely therein.

14. An artificial limb in accordance with claim 13 wherein said first rotator member further comprises at least one additional pin means extending generally parallel to said axis through said circumferential groove, said at least one additional pin means acting as stop means to limit the angle of relative rotation between said first and second rotator members.

15. An artificial limb in accordance with claim 13 wherein said flange is provided on said first rotator member and is substantially disc-shaped, said first rotator member further comprising first and second cylindrical portions projecting coaxially from either side of said flange, one of said cylindrical portions extending within said second rotator member.

16. An artificial limb in accordance with claim 14 wherein said flange is provided on said first rotator member and is substantially disc-shaped, said first rotator member further comprising first and second cylindrical portions projecting coaxially from either side of said flange, one of said cylindrical portions extending within said second rotator member.

* * * * *